United States Patent
Yamamoto (10) Patent No.: US 9,969,562 B2
(45) Date of Patent: May 15, 2018

(54) APPARATUS AND METHOD FOR FOLDING ARTICLES

(71) Applicant: The Procter & Gamble Company, Cincinnati, OH (US)

(72) Inventor: Yoichiro Yamamoto, Cologne (DE)

(73) Assignee: The Procter & Gamble Company, Cincinnati, OH (US)

( * ) Notice: Subject to any disclaimer, the term of this patent is extended or adjusted under 35 U.S.C. 154(b) by 1076 days.

(21) Appl. No.: 13/897,813

(22) Filed: May 20, 2013

(65) Prior Publication Data
US 2013/0248330 A1    Sep. 26, 2013

Related U.S. Application Data (63) Continuation of application No. 13/183,486, filed on Jul. 15, 2011, now Pat. No. 8,469,869.

(60) Provisional application No. 61/364,616, filed on Jul. 15, 2010.

(51) Int. Cl.
B65G 47/00 (2006.01)
A61F 13/15 (2006.01)
B65H 45/04 (2006.01)

(52) U.S. Cl.
CPC ........ B65G 47/00 (2013.01); A61F 13/15747 (2013.01); B65H 45/04 (2013.01); *B65H 2801/57* (2013.01)

(58) Field of Classification Search
CPC ... B65G 47/00; A61G 47/00; A61F 13/15747; B65H 45/04; B65H 2801/57; B31B 2201/2683; B31B 1/36; B31B 1/58; B31B 2201/2637

USPC ................................................ 493/442, 441
See application file for complete search history.

(56) References Cited

U.S. PATENT DOCUMENTS

| | | | | |
|---|---|---|---|---|
| 2,137,978 A | * | 11/1938 | Mills | B41F 13/54 270/37 |
| 2,328,814 A | * | 9/1943 | Laukhuff | A61F 13/2082 493/357 |
| 3,096,977 A | * | 7/1963 | Winkler | B31B 21/00 271/2 |
| 3,689,061 A | | 9/1972 | Nystrand | |

(Continued)

FOREIGN PATENT DOCUMENTS

EP    1 595 517 A1    11/2005
EP    1 726 278 A1    11/2006
(Continued)

OTHER PUBLICATIONS

All Office Actions, U.S. Appl. No. 13/183,486.
(Continued)

*Primary Examiner* — Sameh Tawfik
(74) *Attorney, Agent, or Firm* — Sarah M. DeCristofaro; Abbey A. Lopez (57) ABSTRACT

An apparatus for folding articles advancing in a machine direction including a rotatable roll having a roll surface, at least one protrusion that defines an outermost surface of the roll and at least one pocket that defines an innermost surface of the roll. The apparatus also includes a first and second vacuum conveyor assembly, each comprising two vacuum conveyors. The roll and the vacuum conveyor assemblies are cooperatively configured to fold an article.

19 Claims, 10 Drawing Sheets

(56) References Cited

U.S. PATENT DOCUMENTS

| | | | |
|---|---|---|---|
| 4,425,173 A * | 1/1984 | Frick | A61F 13/15593 112/132 |
| 4,519,597 A * | 5/1985 | DeSanto | B65H 35/08 270/21.1 |
| 4,521,209 A | 6/1985 | DuFresne | |
| 4,548,595 A * | 10/1985 | Heater | B65H 45/04 493/458 |
| 4,694,978 A * | 9/1987 | Westphal | A41B 13/045 223/28 |
| 4,940,464 A | 7/1990 | Van Gompel et al. | |
| 5,092,861 A | 3/1992 | Nomura et al. | |
| 5,167,897 A | 12/1992 | Weber et al. | |
| 5,246,433 A | 9/1993 | Hasse et al. | |
| 5,360,420 A | 11/1994 | Cook et al. | |
| 5,429,578 A * | 7/1995 | Calbrix | B65H 45/168 493/359 |
| 5,460,844 A * | 10/1995 | Gaylor | B65B 29/02 206/5 |
| 5,569,234 A | 10/1996 | Buell et al. | |
| 5,599,335 A | 2/1997 | Goldman et al. | |
| 5,643,588 A | 7/1997 | Roe et al. | |
| 5,674,216 A | 10/1997 | Buell et al. | |
| 5,702,551 A | 12/1997 | Huber et al. | |
| 5,842,964 A | 12/1998 | Huber et al. | |
| 5,897,545 A | 4/1999 | Kline et al. | |
| 5,957,908 A | 9/1999 | Kline et al. | |
| 5,968,025 A | 10/1999 | Roe et al. | |
| 6,009,781 A * | 1/2000 | McNeil | B26D 1/405 83/304 |
| 6,107,537 A | 8/2000 | Elder et al. | |
| 6,118,041 A | 9/2000 | Roe et al. | |
| 6,120,487 A | 9/2000 | Ashton | |
| 6,120,489 A | 9/2000 | Johnson et al. | |
| 6,153,209 A | 11/2000 | Vega et al. | |
| 6,241,232 B1 * | 6/2001 | Schmitt | B65B 63/04 270/30.01 |
| 6,309,336 B1 * | 10/2001 | Muessig | B65H 45/12 493/405 |
| 6,357,505 B1 * | 3/2002 | Jurgens | B65C 9/14 156/564 |
| 6,383,124 B1 * | 5/2002 | St. Germain | B65H 45/165 493/353 |
| 6,385,946 B1 * | 5/2002 | Singh | B65H 35/04 493/416 |
| 6,410,129 B2 | 6/2002 | Zhang et al. | |
| 6,426,444 B2 | 7/2002 | Roe et al. | |
| 6,586,652 B1 | 7/2003 | Roe et al. | |
| 6,617,016 B2 | 9/2003 | Zhang et al. | |
| 6,627,787 B1 | 9/2003 | Roe et al. | |
| 6,705,453 B2 | 3/2004 | Blumenthal et al. | |
| 6,825,393 B2 | 11/2004 | Roe et al. | |
| 6,861,571 B1 | 3/2005 | Roe et al. | |
| 6,888,143 B2 | 5/2005 | Vogt et al. | |
| 6,893,388 B2 | 5/2005 | Reising et al. | |
| 6,915,929 B2 * | 7/2005 | Rauch | D06F 89/00 223/37 |
| 7,216,685 B2 * | 5/2007 | Nakakado | A61F 13/15593 156/494 |
| 7,399,266 B2 | 7/2008 | Aiolfi et al. | |
| 7,407,468 B2 | 8/2008 | Reising et al. | |
| 7,617,656 B2 * | 11/2009 | Wiedmann | A61F 13/15747 493/12 |
| 7,771,337 B2 * | 8/2010 | White | B65H 45/24 493/424 |
| 7,846,082 B2 * | 12/2010 | Burns, Jr. | A61F 13/15764 493/424 |
| 7,955,244 B2 | 6/2011 | Burns, Jr. et al. | |
| 8,257,237 B2 | 9/2012 | Burns, Jr. et al. | |
| 8,276,745 B2 | 9/2012 | Yamamoto | |
| 8,360,231 B2 | 1/2013 | Yamamoto | |
| 8,617,040 B2 * | 12/2013 | Coenen | B65H 45/16 493/442 |
| 2002/0103468 A1 | 8/2002 | Nakakado et al. | |
| 2003/0132549 A1 * | 7/2003 | Mlinar | B26F 3/002 264/293 |
| 2003/0233082 A1 | 12/2003 | Kline et al. | |
| 2006/0276320 A1 * | 12/2006 | Aiolfi | B65B 63/045 493/441 |
| 2009/0094941 A1 * | 4/2009 | Burns, Jr. | A61F 13/15764 53/429 |
| 2009/0098995 A1 | 4/2009 | Burns et al. | |
| 2011/0251040 A1 * | 10/2011 | Yamamoto | A61F 13/15747 493/418 |
| 2012/0015790 A1 * | 1/2012 | Yamamoto | A61F 13/15747 493/442 |
| 2012/0015792 A1 | 1/2012 | Yamamoto | |
| 2012/0238431 A1 * | 9/2012 | Sablone | A61F 13/15747 493/441 |

FOREIGN PATENT DOCUMENTS

| | | |
|---|---|---|
| EP | 1 941 854 A2 | 7/2008 |
| WO | WO 1995/019752 A2 | 7/1995 |
| WO | WO 2008/001209 A2 | 1/2008 |
| WO | WO 2009/032995 A1 | 3/2009 |
| WO | WO 2009/083788 A1 | 7/2009 |

OTHER PUBLICATIONS

All Office Actions, U.S. Appl. No. 13/183,481.
All Office Actions, U.S. Appl. No. 13/183,483.
All Office Actions, U.S. Appl. No. 13/183,490.
All Office Actions, U.S. Appl. No. 13/600,278.

* cited by examiner

APPARATUS AND METHOD FOR FOLDING ARTICLES

CROSS REFERENCE TO RELATED APPLICATIONS

This application is a continuation application of U.S. patent application Ser. No. 13/183,486, filed Jul. 15, 2011, which claims the benefit of U.S. Provisional Application No. 61/364,616, filed Jul. 15, 2010, each of which is hereby incorporated by reference in its entirety.

FIELD OF THE INVENTION

The present disclosure relates to methods and apparatuses for manufacturing articles, and more particularly, to an improved transport roll and method for increasing the rate of article transport, especially during a folding operation.

BACKGROUND OF THE INVENTION

Disposable absorbent articles, such as diapers, pull-on diapers, training pants, adult incontinence pads, wipes, facial tissue, toilet tissue, napkins, paper towels and the like are often manufactured and/or packaged on a high-speed production line where individual articles may move along a production path at a speed of hundreds of meters per minute, and manufacturers of articles are continually trying to increase manufacturing speed. However, in order to increase the speed of a manufacturing process, larger, more powerful drive motors are typically required to increase the operational speed of the various components in the process. Such motors can be costly and take up an undesirable amount of floor space in the manufacturing facility.

In conventional manufacturing processes, it is not uncommon for rolls, sometimes referred to as drums or cylinders, to be used to transport articles from one component or portion of the process to another (e.g., folding drums for bifolding an article). Known folding rolls and/or transport rolls typically have a substantially uniform, two-dimensional, curved surface. An article such as a disposable diaper disposed on the surface of a conventional roll is generally considered to be in a so-called "flat-out" configuration on the roll surface (i.e., no slack in the article which could cause bunching, wrinkles, looseness, or the like). Thus, the number of flat-out articles of a particular length that can be accommodated by a roll may be directly determined by the circumference of the roll. For example, a conventional folding drum having a circumference of 600 mm can accommodate no more than three articles having a length of 200 mm each, assuming the articles do not overlap one another. If the length of each article is increased, for example to 220 mm, and the circumference of the roll is unchanged, then only two articles can be accommodated by the roll per revolution, assuming articles do not overlap. Reducing the size of the articles, for example to 190 mm each, without changing the circumference of the roll may permit the same number of article to be processed, but in instances where the roll is "pitched" (i.e., sized and timed such that the articles are positioned on a particular portion of the roll) then it may be necessary to replace the roll. While it is possible to replace a roll, it may be expensive and time consuming. Increasing the speed of the roll may increase the rate at which articles are processed, but, as pointed out above, it typically requires providing a larger motor, which may not be desirable. In addition, if variable speed servo motors are used, increasing the size of the motor may increase the inertia of the motor and potentially offset the desired speed and/or acceleration benefits.

Accordingly, it would be desirable to provide a process and apparatus for increasing the rate at which articles may be transported on a roll without increasing the size and/or rotational speed of the roll. It would also be desirable to provide a process and apparatus for folding articles and providing substantially aligned end and/or side edges on the folded articles without the use of a mechanical holding means.

SUMMARY OF THE INVENTION

In some aspects, the present disclosure relates to an apparatus for folding articles advancing in a machine direction wherein each article has a leading end and a trailing end. In certain embodiments, the apparatus comprises a rotatable roll comprising a roll surface and an article disposed thereon. The roll surface may include at least one protrusion and at least one pocket. The apparatus may comprise a first vacuum conveyor including a movable surface configured to receive at least a portion of the leading end of the article from the rotating roll. The movable surface of the first vacuum conveyor may be driven by a variable speed motor such that the movable surface of the first vacuum conveyor travels at a first speed when the leading end of the article is received by the first vacuum conveyor and then slows down to a second speed. The apparatus may comprise a second vacuum conveyor including a movable surface for engaging the leading end of the article and applying a peel force thereto such that at least a portion of the leading end of the article is transferred from the first vacuum conveyor to the second vacuum conveyor. The movable surface of the second vacuum conveyor may be driven by a variable speed motor such that after the movable surface of the second vacuum conveyor receives the leading end of the article from the first vacuum conveyor, the second vacuum conveyor speeds up to the first speed while carrying the leading end of the article back to the rotating roll, the second vacuum conveyor being configured to transfer the leading end back to the rotating roll such that the leading end and the trailing end are arranged in a face-to-face relationship to form a folded article.

DETAILED DESCRIPTION OF THE INVENTION

Definitions

"Absorbent article" means a consumer product whose primary function is to absorb and retain soils and wastes, such as devices which are placed against or in proximity to the body of the wearer to absorb and contain the various exudates discharged from the body. Nonlimiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Aligned" means an article in a bifold configuration having an average CD accuracy and an MD accuracy of less than or equal to 3 mm, when measured according to the Alignment Test described in copending U.S. Publication. No. 2009/0098995, titled "System For Bifolding An Absorbent Article," filed by Burns, et al.

"Bifold" means folding an article into two portions. For example, bifolding a disposable diaper may be accomplished by bringing the leading end and the trailing end of the diaper together in a face-to-face configuration on a production line as the article moves in the machine direction of travel, such that the diaper is folded along a fold line into two substantially equal portions. As used herein, a "fold line" is the portion of an article about which the article is folded. The fold line typically extends from one side edge to the opposing side edge in the crotch region and, in certain embodiments, may correspond to the lateral centerline of the article. In certain embodiments, the leading end edge and trailing end edge of an article may be aligned after the article is folded.

"Diaper" or "taped diaper" mean disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Suitable taped diapers are disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

"Disposable" means articles that are generally not intended to be laundered or otherwise restored or reused as absorbent articles (i.e., they are intended to be discarded after a single use and may be recycled, composted or otherwise discarded in an environmentally compatible manner).

"Disposed" means an element(s) is formed (joined and positioned) in a particular place or position as a macro-unitary structure with other elements or as a separate element joined to another element.

"Engage," when used in the context of transferring an article from one carrier to another or from a portion of one carrier to another portion of the same carrier, means coming into close proximity (e.g., <10 cm, up to and including physical contact) such that an engaging force (e.g., suction) present at the surface of the carrier can be applied to an article.

"Holding an article to the surface of a roll" and variations thereof mean employing a holding force to one or more portions of an article in order to join the article at least temporarily to the surface of a roll such that the article is inhibited from traveling in a direction substantially orthogonal to the surface of the roll without reducing or removing the holding force and/or employing a peel-force. This definition is equally applicable to conveyors, e.g., one or more of the conveyor assemblies described herein.

"Joined" means configurations whereby an element is directly secured to another element by affixing the element directly to the other element and to configurations whereby an element is indirectly secured to another element by affixing the element to intermediate member(s) which in turn are affixed to the other element.

"Longitudinal" means a direction running substantially perpendicular from a waist edge to an opposing waist edge of an absorbent article when the article is in a flat out, uncontracted state, or from a waist edge to the bottom of the crotch in a bifolded article. Directions within 45 degrees of the longitudinal direction are considered to be "longitudinal." "Lateral" refers to a direction running from a longitudinal edge to an opposing longitudinal edge of an article and generally orthogonal to the longitudinal direction. Directions within 45 degrees of the lateral direction are considered to be "lateral."

"Machine direction" ("MD") means the direction that is parallel to the direction of travel of an article or article element as it is processed in the forming apparatus. In a folding process such as a bifolding process, it may be possible to have more than one machine direction when an article is undergoing simultaneous processes. In other words, a manufacturing line may have an overall machine direction, but an article may travel in directions other than the overall machine direction as it passes through various process along the manufacturing line. For example, an article having a trailing end portion and a leading end portion, each portion being attached to the surface of a different roll and/or conveyor, may travel in two different directions simultaneously. In this example, both directions of travel may be considered the machine direction. The "cross machine direction" or "cross direction" ("CD") refers to the direction perpendicular to the machine direction and in the plane generally defined by the article or article element.

"Mechanically coupled" means two or more components that, directly or indirectly, act cooperatively to form a mechanism. For example, an electric motor that drives the motion of a gate is said to be mechanically coupled to the gate. The mechanism of operation that mechanically couples the component may be any one of a number of commonly known couplers, including but not limited to: having a shaft extending between the components; a universal joint; a transmission; a linkage; a sprocket and chain; a gear head on one of the components; a gear box; a belt and pulley combination; a clutch mechanism; a spring member; a slider; a pivot; or other known forms of coupling two elements may also be considered mechanical coupling.

"Mechanically secured" means holding an object in place by a mechanical means. For example, a web of material or an absorbent article held to the outer surface of a roll with clips is considered to be mechanically secured. Conversely, holding a web of material or an absorbent article to the surface of a roll with vacuum pressure or centrifugal force is not an example of being mechanically secured.

"Peel force" means the force applied to an object in a direction that is substantially perpendicular to the plane of the surface on which the object rests. A force applied in a direction within 45° of the perpendicular direction may be considered a peel force.

"Training pant(s)" or "pant(s)" mean disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by any suitable technique including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened, front waist fastened, rear waist fastened). Suitable examples of pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

"Vacuum" and "vacuum pressure" mean a pressure of less than 13000 Newtons per square meter.

For ease of understanding, portions of the following description may be exemplified in terms of a disposable absorbent article. However, it is to be understood that while one or more particular examples recited herein may refer to a diaper or training pant, the present invention is not limited to such articles. The folding assembly system described herein may, in fact, be practiced in any situation where an article exhibiting the characteristics described herein is required. Examples of other articles include hard surface cleaning wipes or pads; pre-moistened cloths; paper towels; dryer sheets and dry-cleaning clothes; adult incontinence briefs and undergarments; feminine hygiene garments such as panty liners, absorbent inserts, and the like; toilet paper; tissue paper; personal cleaning wipes or clothes such as baby wipes or facial wipes; packaging components and substrates and/or containers for laundry detergent and coffee, which may be produced in pellets or pouches and may be manufactured in a converting or web process; or even discrete products produced at high speed such as high-speed bottling lines, cosmetics, razor blade cartridges, and disposable consumer batteries.

Figure 1:
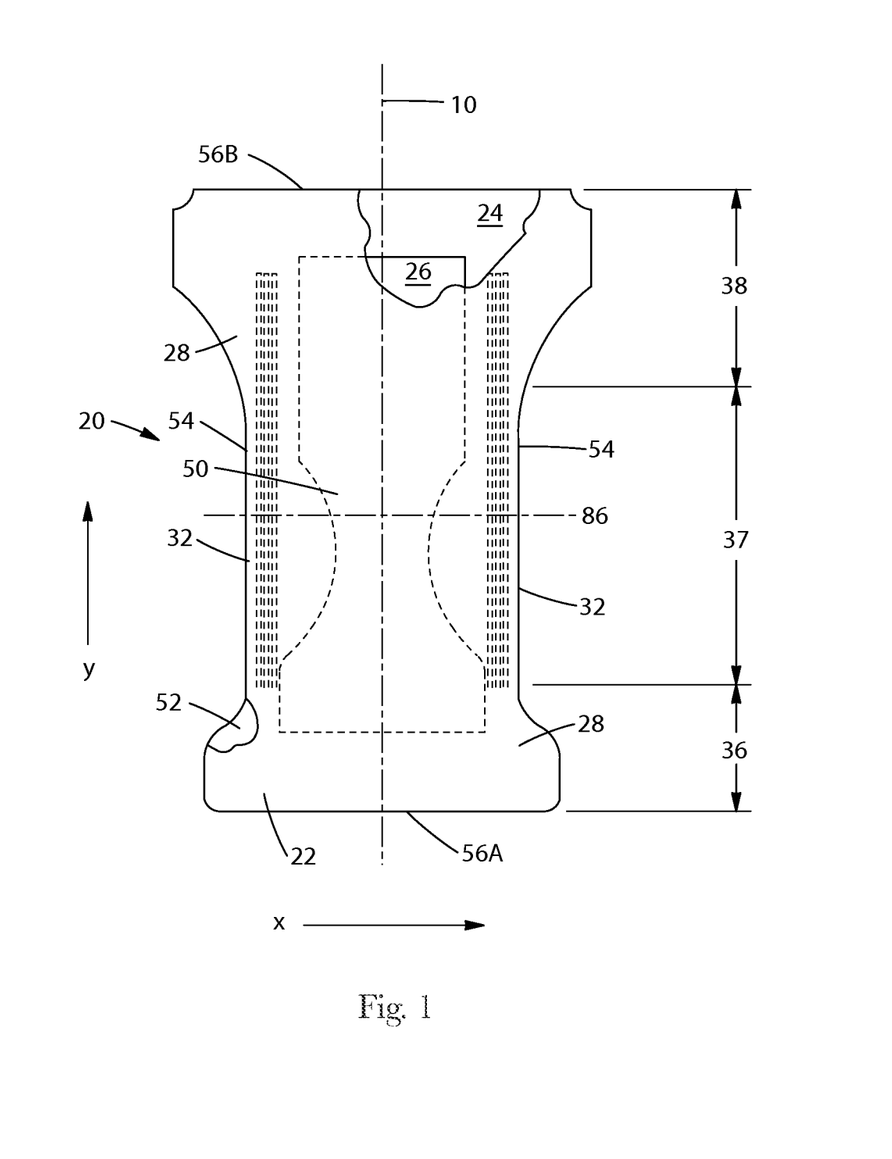
FIG. 1 is a top, plan view of a disposable absorbent article.

FIG. 1 shows a partial cut-away view of a diaper 20 shown in a flat-out, uncontracted state (e.g., with no elastic induced contraction). The diaper 20 may include a body-faceable, liquid pervious topsheet 22 (i.e., faces and/or contacts the body of a wearer when worn as intended); a clothing-faceable, liquid impervious backsheet 24 joined with the topsheet 22 (i.e., faces and/or contacts the clothing of a wearer when worn as intended); an absorbent core 26 positioned between the topsheet 22 and the backsheet 24; side panels 28; and leg cuffs 32. The diaper 20 may further include an outer surface 52 opposed to the inner surface 50, a first waist region 36, a second waist region 38 opposed to the first waist region 36, and a crotch region 37 positioned between the first waist region 36 and the second waist region 38. The diaper 20 may also include longitudinal edges 54, a first end edge 56A corresponding to the first waist region 36, and an opposing second end edge 56B corresponding to the second waist region 38. The diaper 20 may include a longitudinal centerline 10 positioned midway between the longitudinal side edges 54 and a lateral centerline 86 positioned midway between opposing end edges 56A and 56B and orthogonal thereto. The end edges 56A and 56B may be substantially equal in width, as measured from opposing longitudinal side edges 54 to the longitudinal centerline 10, or length, as measured from opposing end edges 56A and 56B to the lateral centerline 86, in order to facilitate folding of the diaper 20, but need not necessarily be so. According to the methods and apparatuses disclosed herein, the diaper 20 may be folded about the lateral centerline 86 such that the first waist region 36 and the second waist region 38 are positioned in a face-to-face relationship along the inner surface 50 (e.g., in a bifolded configuration). A folded diaper according to certain embodiments may have the first end edge 56A and the second end edge 56B aligned. A folded diaper according to certain embodiments may have the longitudinal side edges 54 partially or entirely aligned (e.g., the longitudinal side edges 54 may be aligned only in those areas that are visible to a consumer and/or are to be permanently joined together).

Figure 2:
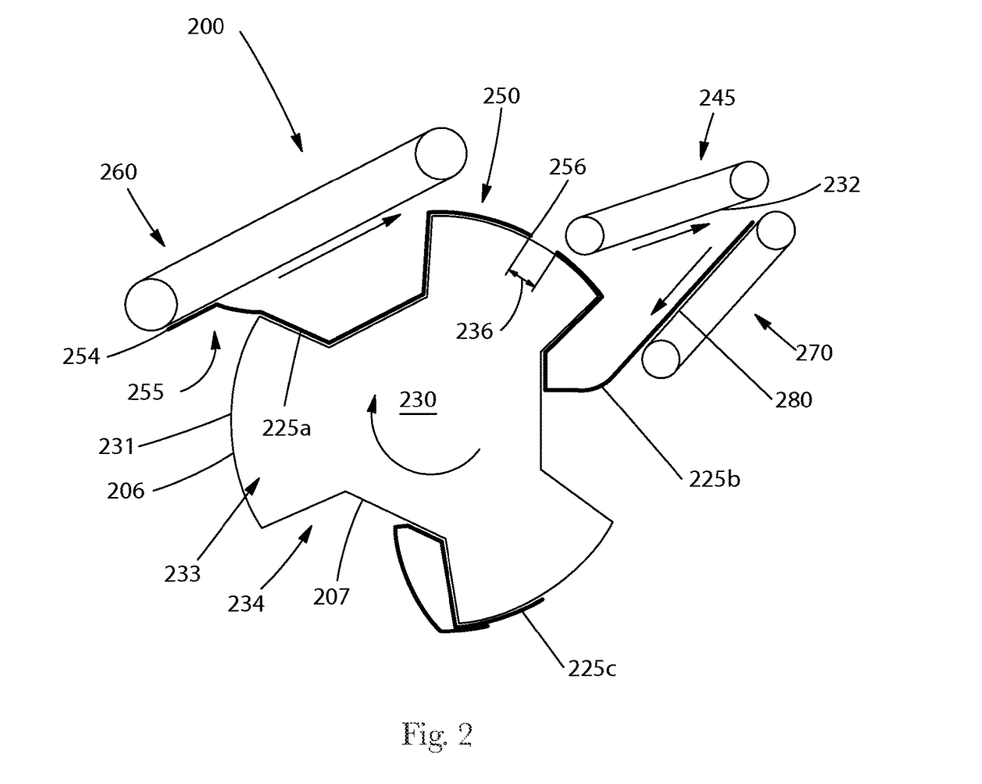
FIG. 2 is schematic side view of an embodiment of the apparatus and method disclosed herein.
Figure 9:
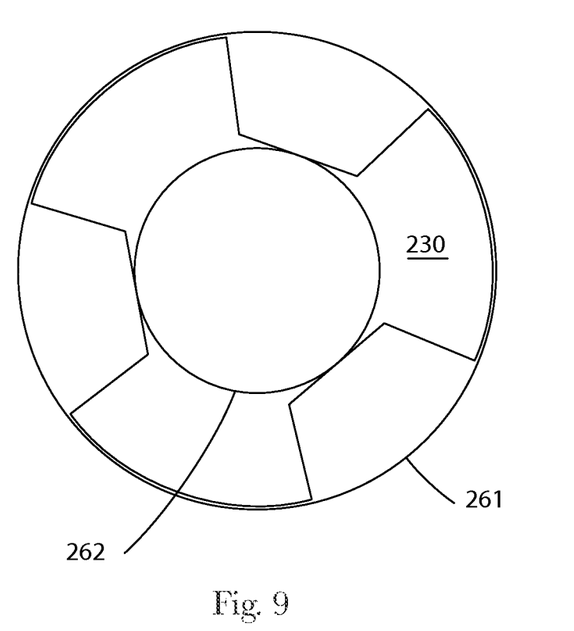
FIG. 9 is a schematic side view of an embodiment of the apparatus disclosed herein.

FIG. 2 shows an exemplary embodiment of a folding apparatus 200 that includes a folding drum 230, a peel conveyor assembly 245, and a folding conveyor assembly 270. In certain embodiments, the folding drum 230 may be configured as a commonly known vacuum drum (i.e., drum that is configured to apply vacuum/suction at one or more portions of its surface). The surface 231 of the folding drum 230 is defined by an alternating series of pockets 234 and protrusions 233. Some or all of the pockets 234 and/or protrusions 233 may be extend the full width of the surface 231 of the folding drum 230 in the CD, such that the profile of the folding drum 230 appears "gear-like." In certain embodiments, some or all of the pockets 234 and/or protrusions 233 may extend only partially across the folding drum 230 in the CD. The protrusions 233 and/or pockets 234 may be configured to hold the article 225 to the surface 231 of the folding drum, for example, with vacuum. Suitable folding drums 230 for use herein may include any number of protrusions 233 and/or pockets 234, as desired. It is to be understood that the terms protrusion 233 and pocket 234 are relative terms, which are used to conveniently describe the unique, contrasting surface features of the folding drum 230 disclosed herein. The protrusions 233 and pockets 234 may be uniformly sized such that all the pockets are sized the same and/or all of the protrusions are sized the same. Alternatively, some or all the protrusions and/or pockets may be of different sizes. Suitable examples of pockets sizes include a depth (i.e., the distance that the pocket 234 extends away, orthogonally, from the outermost surface of a protrusion 233) of between 10 and 150 mm, 20 and 100 mm, 30 and 80 mm, or even 60 mm. While not particularly limited, the pockets 234 may be sized according the article and/or portion of the article to be placed in the pocket. The protrusions 233 may define the outermost portion 206 of the surface 231 and the outer circumference 261 of the folding drum 230, as shown in FIG. 9, while the pockets 234 define an innermost portion 207 of the surface 231 and an inner circumference 262. The number of protrusions 233 and pockets 234 present on the folding drum 230 depends on the number of articles to be accommodated by the folding drum 230 (e.g., at least one pocket 234 and at least one protrusion 233 may be required for each article to be accommodated). The protrusions 233 and/or pockets 234 may have relatively uniform surfaces (e.g., smooth). But in certain embodiments, some or all of the pockets 234 and/or protrusions 233 may include surface features such as corrugations, fingers, channels, rough portions, smooth portions, raised portions, lowered portions and the like, for example, to aid in holding and/or transferring an article 225 to and/or from the surface 231 of the folding drum 230.

In certain embodiments (e.g., when the absorbent article 225 is in the form of a disposable diaper or pant), the absorbent article 225 (e.g., article 225a, 225b, or 225c) may be transferred to the surface 231 of the folding drum 230 such that the topsheet of the absorbent article 225 is facing outward and the backsheet of the absorbent article 225 is held against the surface 231 of the folding drum 230. The absorbent article 225 may be oriented in relation to a predetermined path to provide a leading end portion 250 positioned downstream of a trailing end portion 255. The leading end 250 of the article 225 may be transferred from the transfer apparatus 260 to a protrusion 233 on the folding drum 230. As the folding drum 230 rotates, a protrusion 233 will become positioned proximate to the transfer apparatus 260 such that the leading end 250 of the absorbent article 225 can be transferred to the protrusion 233 (e.g., by applying a peel force to the leading end 250). After the leading end 250 is transferred to the protrusion 233, a holding force (e.g., vacuum) may be applied to the leading end 250 to secure it to the surface 231 of the folding drum 230. In certain embodiments, one or more portions of the article 225 (e.g., the middle portion) may be mechanically secured to the surface 231 of the folding drum 230, for example, with movable bifold clamps such as those described in copending U.S. Ser. Nos. 12/203,339 and 61/322,333. As the folding drum 230 continues to rotate, the absorbent article 225 continues to be transferred from the transfer apparatus 260 to the folding drum 230 until the entire absorbent article 225 is disposed on the folding drum 230. The absorbent article 225 may be disposed on the folding drum 230 such that a first portion of the article (e.g., the leading end portion 250) is disposed on a first protrusion 233 ("leading protrusion"), the middle portion of the absorbent article 225 is disposed in the pocket 234 adjacent the leading protrusion, and a third portion of the disposable article (e.g., the trailing end portion 255) is disposed on a second protrusion 233 ("trailing protrusion"). In certain embodiments, it may be desirable to provide at least some slack in the article 225 to facilitate transferring a portion of the article 225 (e.g., the middle portion) to the pocket 234. For example, if an article is transferred to the folding drum with no slack, as in a conventional process (i.e., in an extended flat out configuration), the article may be stretched over the pocket 234 like a cover, instead of being placed within the pocket 234. However, it is to be understood that, in certain embodiments, a portion of an article in a flat-out configuration may be placed in a pocket 234 by positioning the transfer apparatus closer to the inner surface 207 of the pocket 234 and/or providing sufficient vacuum at the inner surface 207 of the pocket 234 to pull the article portion into the pocket 234. Further, the holding force exerted by the transfer apparatus 260 may be reduced, removed, or even reversed (e.g., from negative pressure to positive pressure) to facilitate placement of the article portion within the pocket 234. Still further, a portion of the article 225 may be transferred to the pocket 234 mechanically, for example, by using hooks; loops; pistons; clips; clamps; fingers, pins; combinations of these and the like or any other suitable mechanical transfer means known in the art. Since the folding drum 230 typically rotates continuously, a leading protrusion may include both the leading end 250 of one article and the trailing end of another article 225. Thus, it may be desirable to provide a suitable space 236 between the leading edge 250 of a first absorbent article 225a and the trailing edge 255 of a second absorbent article 225b (e.g., between 1 and 200 mm apart; 2 and 100 mm; 5 and 80 mm; or even between 10 and 50 mm) which are disposed on the same protrusion 233, as shown in FIG. 2. In certain embodiments, the transfer apparatus 260 may be configured to provide suitable spacing between the articles 225. Examples of a suitable transfer apparatus may be found in U.S. Ser. No. 61/364,626, titled Method and Apparatus For Transferring Articles of Different Sizes, filed Jul. 15, 2010 by Yamamoto, et al., as U.S. Pat. No. 6,705,453 to Blumenthal, et al., on Mar. 16, 2004.

After the article 225 is transferred to the folding drum 230, the leading end 250 of the article 225, which is disposed on a protrusion 233, may be carried toward the peel conveyor assembly 245 at a first speed $V_1$. The peel conveyor assembly 245 may include a vacuum conveyor 245 with a movable surface 232. The folding drum 230 and the peel conveyor assembly 245 may be positioned to provide a suitable distance between the surface 231 of the folding drum 230 and the movable surface 232 of the peel conveyor assembly 245 such that an article 225 disposed on the surface 231 of the folding drum 230 can pass by the peel conveyor surface 232 with little or no resistance. For example, as the trailing end 255 of the article 225 approaches the peel conveyor assembly 245, the trailing end 255 may pass by without contacting the movable surface 232 or even come into contact with the movable surface 232, as long as the contact does not substantially impede the advancement of the absorbent article 225 in the MD. In certain embodiments, the peel conveyor assembly 245 may be configured to peel or remove at least a portion of the leading end 250 of the absorbent article 225 from the outer surface 231 of the folding drum 230 at the first speed $V_1$ (i.e., the speed at which the leading end 250 is travelling) and slow the leading end 250 to a second speed $V_2$ (i.e., $V_2<V_1$).

The peel conveyor assembly 245 may transfer the leading end 250 to the folding conveyor assembly 270 at the second speed $V_2$. In certain embodiments, the speed and/or direction of the folding conveyor 270 may be adjusted to match the speed and/or direction of the peel conveyor 245 when the leading end 250 is transferred. For example, the movable surface 280 of the folding conveyor assembly 270 may be travelling in the same direction (i.e., away from the folding drum 230) and at substantially the same speed (e.g., within 1%, 2%, 3%, 4%, or even 5%) as the movable surface 232 of the peel conveyor assembly 245. In this example, after the leading end 250 is transferred to the folding conveyor assembly 270, the direction and/or speed of the movable surface 280 of the folding conveyor 270 may be changed such that the leading end 250 is carried back toward the folding drum at the first speed $V_1$. The folding conveyor assembly 270 may include a vacuum conveyor 270 with a movable surface 280. The folding drum 230 and the folding conveyor assembly 270 may be positioned to provide a suitable distance between the surface 231 of the folding drum 230 and the movable surface 280 of the folding conveyor assembly 270 such that an article 225 disposed on the surface 231 of the folding drum 230 can pass by the folding conveyor surface 280 with little or no resistance. The folding conveyor assembly 270 may accelerate the leading end 250 back to the first speed $V_1$ and transfer the leading end 250 back to the folding drum 230. In this way, the leading end 250 and the trailing end 255 may be traveling at substantially the same speed when the two portions 250, 255 are brought together in a face-to-face relationship to provide a folded article 225c. The folded article 225c may then be subjected to one or more additional, optional processes such as a commonly known process for permanently and/or refastenably joining the front and back side panels of the article 225 to one another to form a disposable pant or a pre-fastened disposable pant. Exemplary methods for seaming, inspecting, and tucking an article to form a pre-fastened pant are disclosed in U.S. Pat. No. 6,888,143, issued to Vogt, et al.

Figure 3A:
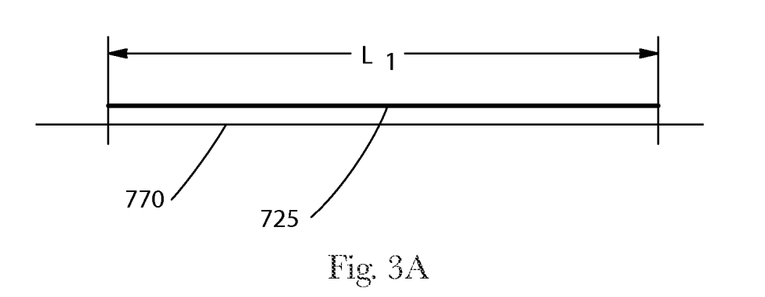
FIGS. 3A and 3B are cross-section views of an article supported on a surface.
Figure 3B:
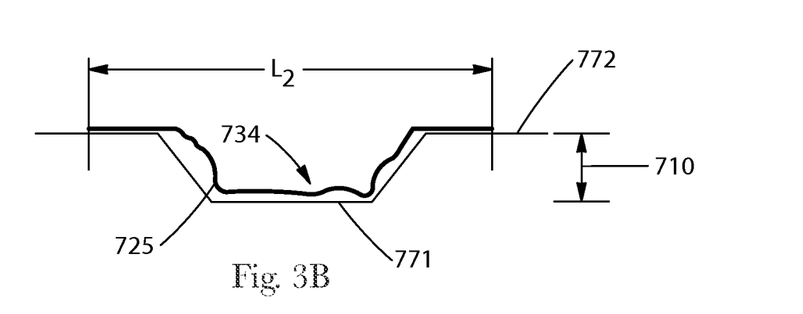

By providing a folding drum 230 with pockets 234, a portion of the absorbent article 225 (e.g., the middle portion) may be desirably positioned in the pocket 234, thereby reducing the distance between the leading end edge 256 and the trailing end edge 254 and effectively reducing the length of the article 250. FIGS. 3A and 3B illustrate how placing a portion of an article in a pocket may reduce the overall length of the article being supported on a surface. Thus, the length of an article can be adjusted to match the pitch of the drum, which may eliminate the need to replace the drum when manufacturing articles of different lengths. FIG. 3A shows an article 725 disposed on a flat surface 770. The article 725 has a length $L_1$, which is disposed entirely on the flat surface 770. FIG. 3B shows the article 725 of FIG. 3A disposed on a surface that includes a pocket 734 having a depth 710. As can be seen in FIG. 3B, part of the article 725 is disposed on an outer surface portion 772 and part of the article 725 is disposed in the pocket 734 on the inner surface portion 771. Thus, the length $L_2$ of the article 725 disposed on the outer surface 772 shown in FIG. 3B is less than the length $L_1$ of the article disposed on the surface 700 shown in FIG. 3A, by up to two times the depth 710 of the pocket 734 or more. For example, if the pocket has a depth of 60 mm, the length $L_2$ of the article 725 supported on the outer surface 772 may be approximately 120 mm less than the length $L_1$ of the article disposed on the flat surface 770.

Figure 4:
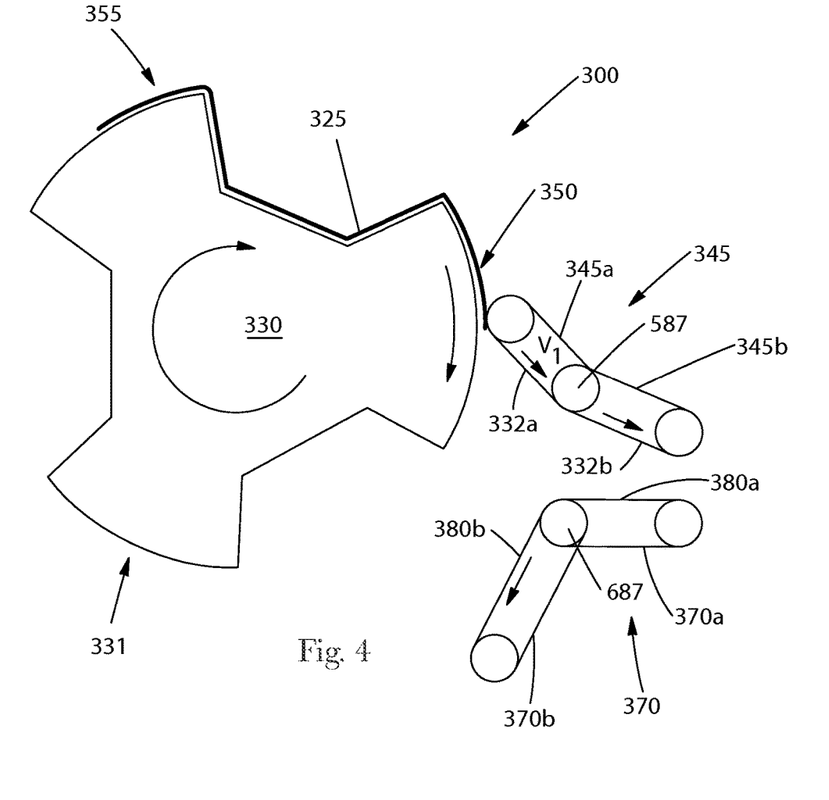
FIGS. 4-8 are schematic side views of an embodiment of the apparatus and method disclosed herein.

FIG. 4 shows an exemplary embodiment of a folding system 300 that includes a rotatable folding drum 330, a peel conveyor assembly 345 and a folding conveyor assembly 370. The folding drum 330 may be configured as one or more of the folding drums described herein, having a surface 331 for carrying an article 325. The peel conveyor assembly 345 may include a first peel conveyor 345a and a second peel conveyor 345b, and each peel conveyor 345a, 345b may include a movable surface 332a, 332b. For example, the first and/or second movable surface 332a, 332b of the peel conveyor assembly 345 may include a movable foraminous conveyor belt configured in an endless loop. In certain embodiments, the first peel conveyor movable surface 332a may move at a single speed, while the second peel conveyor movable surface 332b may be configured to travel at the same speed as the first movable surface 332a and at one or more slower second speeds, including a speed of zero. In other embodiments, the first and second peel conveyor movable surfaces 332a, 332b may both be configured to move at two or more speeds. In certain embodiments, the first and second peel conveyors 345a, 345b may share one or more common elements such as, for example, a shaft 587. Shaft 587 may be coupled to, e.g., a constant or variable speed motor and configured to drive the endless belt 332b of the second peel conveyor 345b at one or more speeds. The shaft 587 may also include one or more free-spinning rollers or pulley-like elements that enable the shaft 587 to simultaneously operate as an idler roll for the endless belt 332a of the first peel conveyor 345a. By sharing shaft 587, the first and second peel conveyors 332a and 332b may be configured to overlap at one end in the machine direction, and thereby facilitate transfer of an article from the first peel conveyor 345a to the second peel conveyor 345b. While the first and second conveyors 345a, 345b in the foregoing example may share a common element, it is to be understood that the first and second conveyors 345a, 345b may also be configured as discrete components.

The folding conveyor assembly 370 may include a first folding conveyor 370a and a second folding conveyor 370b. The first and second folding conveyor 370a, 370b may each include a movable surface 380a, 380b for receiving an article from the peel roll assembly 245 and securely carrying it back toward the folding drum 330. In certain embodiments, the first and second folding conveyors 370a, 370b may share one or more common elements such as, for example, a shaft 687. Shaft 687 may be coupled to, e.g., a variable speed drive motor and configured to drive the endless belt 380a of the first folding conveyor 370a at one or more speeds. The shaft 687 may also include one or more free-spinning rollers or pulley-like elements that enable the shaft 687 to simultaneously operate as an idler roll for the endless belt 380b of the second folding conveyor 370b. The second folding conveyor 370b may be driven by, e.g., a constant speed motor that drives the second folding conveyor belt 380b at, e.g., the surface speed of the folding drum 330, through a mechanical coupling. By sharing shaft 687, the first and second folding conveyor belts 380a, 380b may be configured to overlap at one end in the machine direction, and thereby facilitate transfer of an article from the first folding conveyor 370a to the second folding conveyor 370b. While the first and second folding conveyors 370a, 370b may share a common element, it is to be understood that the first and second folding conveyors 370a, 370b may also be configured as discrete components. It is also to be appreciated that, in certain embodiments, the second conveyor 370b may be configured as a variable speed conveyor.

Referring to FIGS. 4-8, an exemplary process for folding an article with the folding system 300 is described. As shown in FIG. 4, the folding drum 330 rotates to position the leading end 350 of the article 325 proximate the peel conveyor assembly 345 at speed $V_1$. Thus, in certain embodiments, it may be desirable to configure the movable surface 332a of the first peel conveyor 345a to travel at or approximately speed $V_1$, e.g., within 0.5%, 0.2%, 0.1%, or even identical to the surface speed of the folding drum 330.

Figure 5:
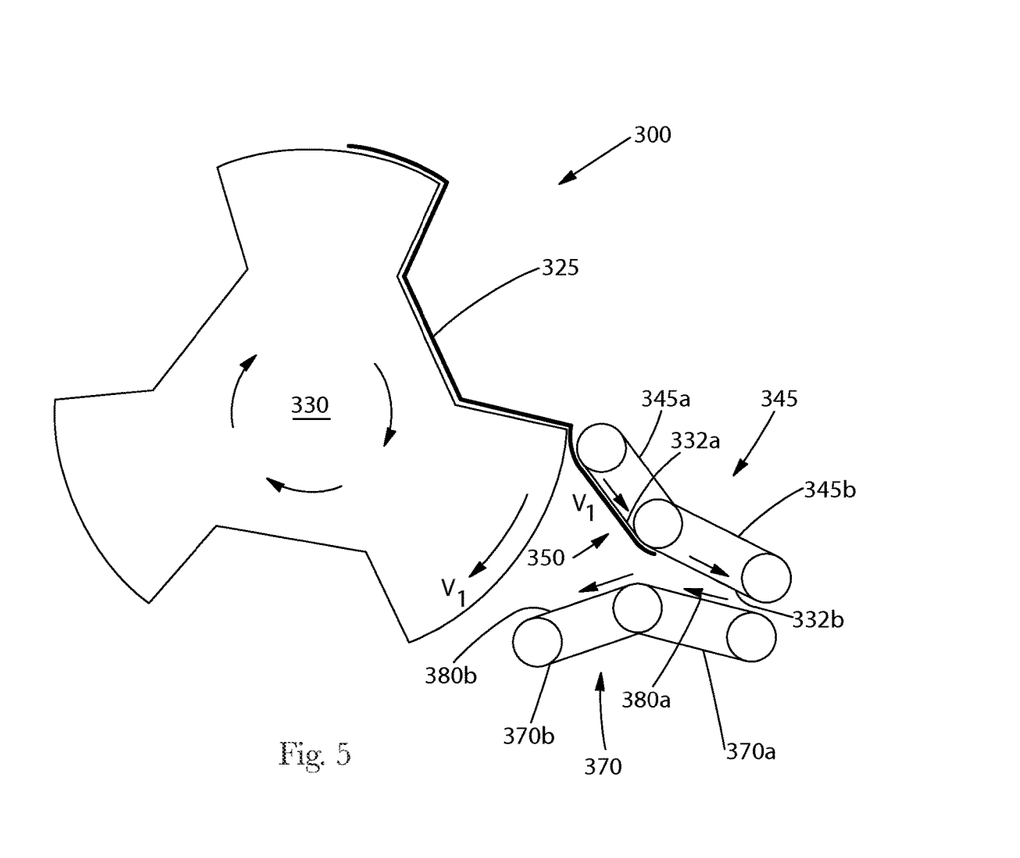

As the leading end 350 of the article 325 approaches the peel conveyor assembly 345, at least a portion of the leading end 350 may be transferred and secured to the movable surface 332a of the first peel conveyor 345a, as shown in FIG. 5. Any force exerted by the folding drum 330 on the leading end 350 (e.g., suction/vacuum/mechanical) may be simultaneously or sequentially removed or reduced as the leading end 350 is peeled from the folding drum 330. After receiving the leading end 350 of the absorbent article 325 from the folding drum 330, the first peel conveyor 345a transports the leading end 350 towards the movable surface 332b of the second peel conveyor 345b and transfers it thereto. At the time of transfer, the speed of the second peel conveyor 345b may substantially match the speed of the first peel conveyor 345a (e.g., speed $V_1$). But after at least a portion of the leading end 350 has been transferred to the second peel conveyor 345b, the speed of the second peel conveyor 345b may be decreased to a second slower speed $V_2$, in preparation for transferring the leading end 350 of the article 325 to the folding conveyor assembly 370.

Once the leading end 350 reaches a particular portion of the peel conveyor assembly 345 (e.g., at or near the end of the second peel conveyor 345b) and/or reaches a desired speed (e.g., $V_2$), the leading end 350 may be transferred to the folding conveyor assembly 370. In preparation for the transfer, the first folding conveyor surface 380a and/or the second peel conveyor surface 332b may be slowed or even temporarily stopped prior to, during, and/or after engagement of the leading end 350 by the first folding conveyor surface 380a. In certain embodiments, the direction in which the movable surfaces 332b, 380a of the second and/or third vacuum conveyors 345b, 370a are travelling may be changed such that the movable surfaces 332b, 380a are travelling in the same direction at substantially the same speed when the leading end 350 is transferred. Upon engaging the leading end 350, the folding conveyor assembly 370 may be configured to apply sufficient peel force (e.g., suction) to the leading end 350 to overcome the holding force of the peel conveyor assembly 345. In certain embodiments, it may be desirable to reduce or remove the holding force exerted by the peel conveyor assembly 345 on the absorbent article 325 or portions thereof when the absorbent article 325 reaches a desired position or when the folding conveyor assembly 370 engages the leading end 350.

In some instances, the first folding conveyor surface 380a may be traveling in a direction and/or speed that are different from the second peel conveyor surface 332b. Thus, in order to reduce the possibility of such premature engagement or contact of the first folding conveyor 370a with the second peel conveyor 332b and/or leading end 350, a suitable distance or gap may be provided between the second peel conveyor surface 332b and the first folding conveyor surface 380a. In certain embodiments, one or both of the movable surfaces 380a, 380b of the folding conveyor assembly 380 may be repositionable relative to the peel conveyor assembly 345 and/or folding drum 330 via a positioning mechanism mechanically coupled to the folding conveyor assembly 370. Similarly, in certain embodiments, one or both of the movable surfaces 332a, 332b of the peel conveyor assembly 345 may be repositionable relative to the folding conveyor assembly 370 and/or folding drum 330 via a positioning mechanism mechanically coupled to the peel conveyor assembly 345. A suitable positioning mechanism may be configured to automatically vary the distance between the first movable surface 380a of the folding conveyor assembly 370 and the second movable surface 332b of the peel conveyor assembly 345 in a continuous or intermittent fashion. Such positioning mechanisms may include for example, one or more cams, pistons, gears, pulleys, and the like. The positioning mechanism may be configured to suitably position the first folding conveyor 370a to engage the leading end 350 during the "upstroke" (i.e., when the movable surface 380a of the first vacuum conveyor 370a is being moved closer to the movable surface 332b of the second conveyor 345b) and to provide a suitable gap between the vacuum conveyor 380 and the peel conveyor 345 during the "downstroke" (i.e., when the movable surface 380a of the first vacuum conveyor 370a is being moved away from the movable surface 332b of the second conveyor 345b), as suitably exemplified in U.S. Ser. No. 61/322,333. Additionally or alternatively, the position of the movable surface 332b of the second conveyor 345b may be moved relative to the movable surface 380a of the first conveyor 370a. The positioning mechanism may have any suitable stroke length desired, for example, a stroke length of greater than 1 mm, between 1 mm and 20 cm, 1 mm and 20 mm, 1 mm and 10 mm, or even 1 mm and 5 mm, which provide a gap distances that is at least greater than the thickness of the absorbent article 325, for example, greater than 1 mm, between 1 mm and 20 cm, or even between 1 mm and 20 mm. One particular example for providing a gap includes using a cam with a 3 mm stroke length to continuously varying the position of the first folding conveyor surface 380a relative to the second peel conveyor surface 332b. In certain embodiments, it may be desirable to vary or hold constant the distance between the surface 331 of the folding drum 330 and one or more of the movable conveyor surfaces 332a, 332b, 380a, 380b. In certain embodiments, the movement of the first folding conveyor 370a may pause at a particular position during the bifold process, for example, at the "top of the upstroke" (i.e., when the distance between the first folding conveyor surface 380a and the second peel conveyor surface 332b is at a minimum), the "bottom of the downstroke" (i.e., when the distance between the first folding conveyor surface 380a and the second peel conveyor surface 332b is at a maximum), and/or upon engaging the leading end 350. In a particularly suitable embodiment, the first folding conveyor 370a may pause at the top of the upstroke with simultaneously engaging the leading end 350.

Figure 6:
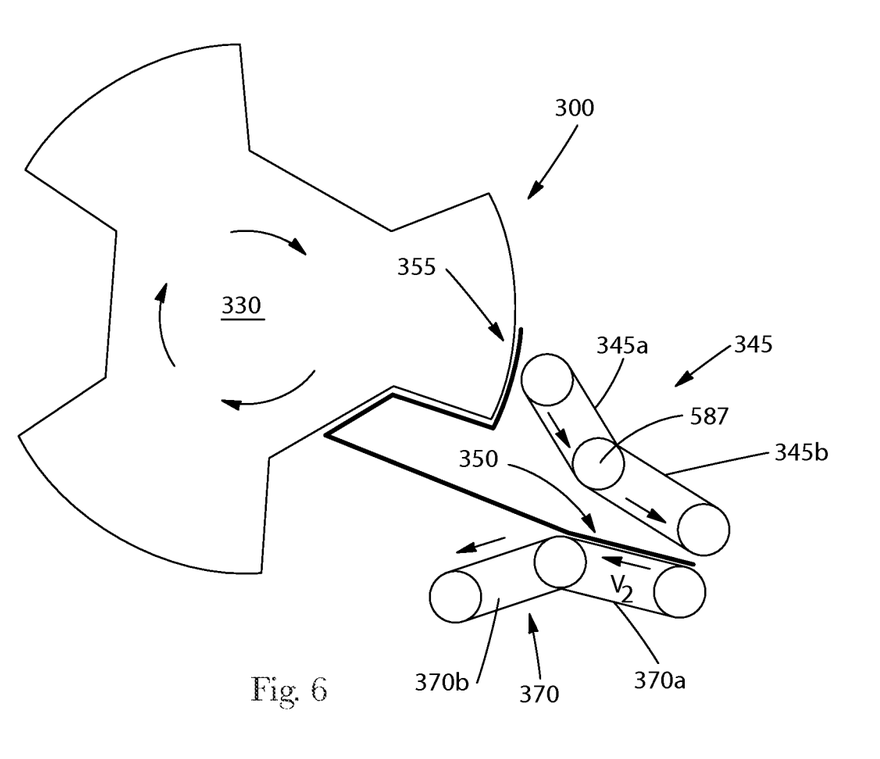
Figure 7:
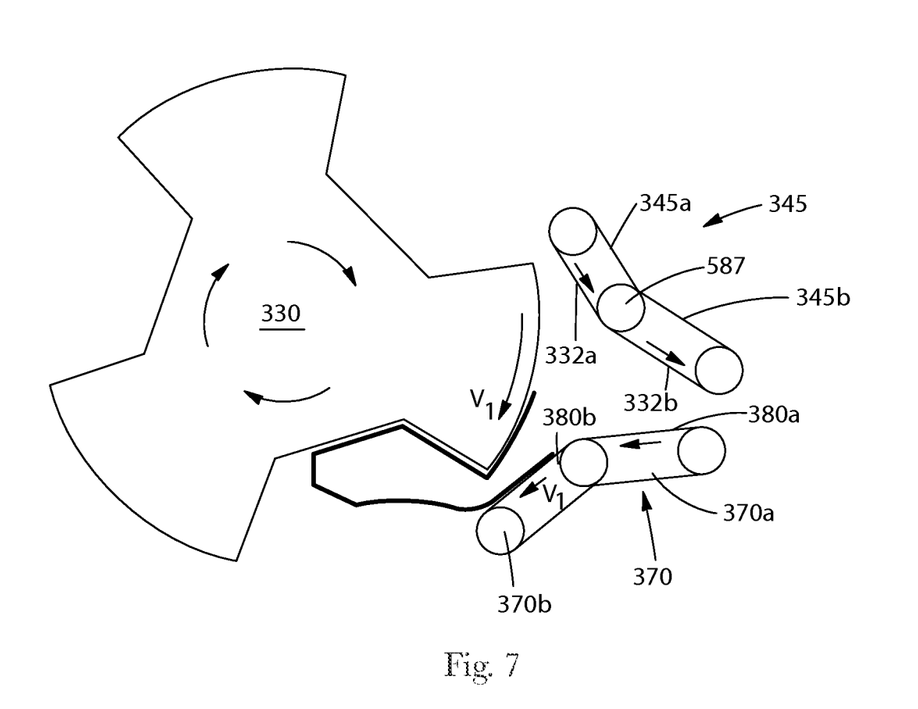
Figure 8:
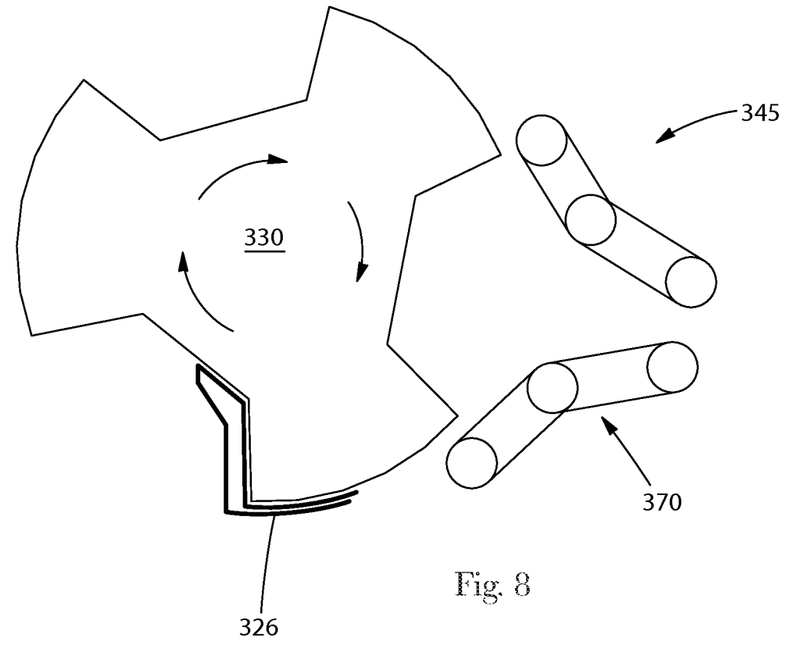

As shown in FIG. 6, once the leading end 350 has been transferred to the folding conveyor assembly 370, the folding conveyor assembly 370 is sped up to the first speed $V_1$ and carries the leading end 350 back towards the folding drum 330 to be placed in a face-to-face relationship with the trailing end portion 355. For example, the leading end 350 may be received by the movable surface 380a of the first folding conveyor 370a at the second speed $V_2$ and sped up to speed $V_1$. The leading end 350 is then be transferred to the moving surface 380b of the second folding conveyor 270b, which is moving at the first speed $V_1$ toward the folding drum 330, as shown in FIG. 7. As shown in FIG. 8, the leading end 350 is transferred from the second folding conveyor 380b back to the folding drum 330 to provide a bifolded article 326, which can then be subjected to additional, optional process such as adhesive and/or high pressure bonding or pre-fastening, for example, to form a pant product.

In certain embodiments, the first and second movable surfaces 380a and 380b of the folding conveyor assembly 370 may each be driven by a variable speed motor. In such an embodiment, after engaging the leading end 350, the movable surface 380a of the first bifold conveyor 370a may be sped up to a third speed $V_3$ that is faster than the second speed $V_2$ but slower than the first speed $V_1$ (i.e., the speed at which the trailing end 355 of the article is travelling). Continuing with this example, the second bifold conveyor 370b may accelerate the leading end 350 from the third speed $V_3$ to the first speed $V_1$. In this way, the leading end 350 and the trailing end 355 may be traveling at substantially the same speed when the two portions 350, 355 are brought together in a face-to-face relationship.

Figure 10:
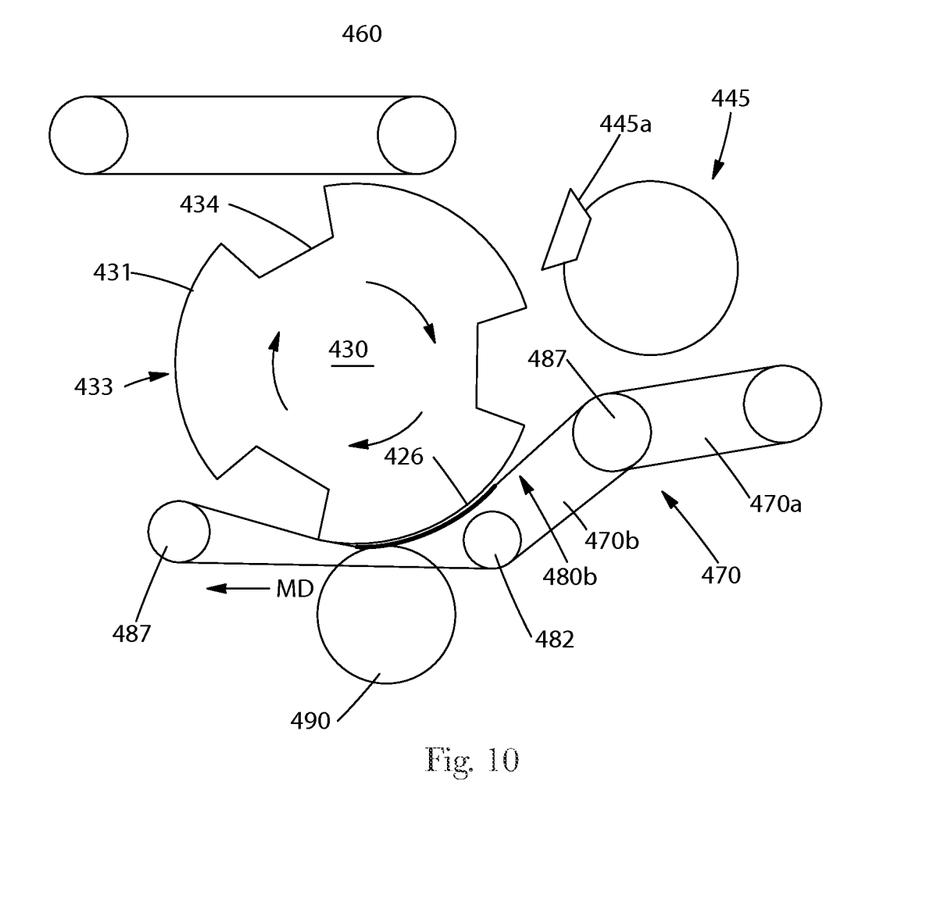
FIG. 10 is a schematic view of an embodiment of the apparatus and method disclosed herein.

FIG. 10 shows an exemplary embodiment of a folding system 400 that includes a rotatable folding drum 430, a peel assembly 445 and a folding assembly 470. The folding drum 430 includes a surface 431 defined by alternating pockets 434 and protrusions 433. An article may be fed to the folding system 400 via a transfer apparatus 460 such as one or more of the transfer apparatuses described herein. The article may be carried around the surface 431 of the folding drum 430 toward the peel assembly 445 and the folding assembly 470 as the folding drum 430 rotates. The peel assembly 445 and folding assembly 470 may each be configured to include a single vacuum conveyor belt, two or more vacuum conveyor belts, or a roll with one or more moving heads. As shown in FIG. 10, the peel assembly 445 includes a roll with a moving head 445a. The folding system 400 shown in FIG. 10 also includes a folding assembly 470 that includes a first and second folding conveyor 470a, 470b. The first folding conveyor 470a may be configured to receive the leading end portion of a disposable absorbent article from the peel assembly 445 and transport it to the second folding conveyor, as described above. The first and second folding conveyors 470a, 470b may share a common element such as shaft 487 to facilitate transfer of an article or article portion. The second folding conveyor 470b receives the article portion and transports it toward the folding drum 430. As the folding drum 430 rotates, the leading and trailing end of an article disposed on the drum surface 431 are brought together in a face-to-face relationship to form a folded article 426. As shown in FIG. 10, the movable surface 480b of the second folding conveyor 470b may be extended to transport the folded article 426 to one or more downstream process such as a seaming process 490. As the folded article 426 advances in the MD, it may be disposed between the movable surface 480b of the second folding conveyor 470b and the surface 431 of the folding drum 430. In this way, the folded article 426 and/or article components may be less likely to become undesirably repositioned prior to reaching the seaming station 490. The second folding conveyor 470b may include one or more idler rolls 482 to help control the tension in the extended belt 480b, and may be driven by one or more constant or variable speed drive motors 487.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for transporting articles advancing in a machine direction, wherein each article has a leading end portion and a trailing end portion, the apparatus comprising:
   a rotatable roll rotating at a roll speed, the rotating roll comprising a roll surface and an article disposed thereon, the roll surface including at least one protrusion and at least one pocket, wherein the article is disposed on the roll surface, wherein at least a portion of the article is placed in the at least one pocket and at least a portion of the article extends onto the at least one protrusion;
   a first conveyor assembly comprising a first vacuum conveyor and a second vacuum conveyor, each of the first and second vacuum conveyors including a movable surface, wherein the movable surface of the first vacuum conveyor travels at a first speed and receives the leading end portion of each article from the rotating roll, and wherein the movable surface of the second vacuum conveyor travels at the first speed and at a second speed and receives the leading end portion of each article from the first conveyor; and
   a second conveyor assembly comprising a third vacuum conveyor and a fourth vacuum conveyor, each of the third and fourth vacuum conveyors comprising a movable surface, wherein the movable surface of the third conveyor travels at the second speed and at the first speed and receives the leading end portion of each article from the second vacuum conveyor, and wherein the movable surface of the fourth vacuum conveyor travels at the first speed and receives the leading end portion of each article from the third conveyor,
   wherein the pocket is sized and imparts a bifold in the article in conjunction with manipulation of the article by the first conveyor assembly and the second conveyor assembly.

2. The apparatus of claim 1, wherein the movable surface of the second conveyor is travelling at the first speed when the leading end is transferred from the first conveyor to the second conveyor and wherein the movable surface of the second conveyor is travelling at the second speed when the leading end is transferred from the second conveyor to the third conveyor.

3. The apparatus of claim 1, wherein the second speed is less than the first speed.

4. The apparatus of claim 1, wherein vacuum is present at the movable surface of the third conveyor such that a peel force is applied to the leading end portion of the article when the leading end portion is proximate to the movable surface of the third vacuum conveyor, and the peel force is sufficient to transfer the leading end portion from the surface of the second conveyor to the surface of the third conveyor.

5. The apparatus of claim 1, wherein the positioning mechanism is mechanically coupled to the movable surface of the third vacuum conveyor.

6. The apparatus of claim 1, wherein the first vacuum conveyor is mechanically coupled with the second vacuum conveyor, wherein the third vacuum conveyor is mechanically coupled with the second vacuum conveyor.

7. The apparatus of claim 1, wherein the fourth vacuum conveyor is configured to transfer the leading end portion of each article back to the rotating roll.

8. The apparatus of claim 1, wherein the pocket has a depth of between 10 millimeters and 150 millimeters.

9. The apparatus of claim 1, wherein the first vacuum conveyor and the second vacuum conveyor share a common rotatable shaft.

10. The apparatus of claim 1, wherein at least one of the first and second conveyor assemblies includes a positioning mechanism for changing a distance between the movable surfaces of the second and third vacuum conveyors.

11. An apparatus for transporting articles advancing in a machine direction, the apparatus comprising:
    a roll rotatable at a roll speed, the roll comprising a roll surface, the roll surface including at least one protrusion and at least one pocket, wherein at least a portion of an article is placed in the at least one pocket and at least a portion of the article extends onto the at least one protrusion;
    a first conveyor assembly comprising a first vacuum conveyor mechanically coupled with a second vacuum conveyor, each of the first and second vacuum conveyors including a movable surface, wherein the movable surface of the first vacuum conveyor travels at the first speed, wherein the first vacuum conveyor is positioned proximate to the roll surface, and wherein the movable surface of the second vacuum conveyor travels at the first speed and at a second speed, wherein the second speed is different from the first speed; and
    a second conveyor assembly comprising a third vacuum conveyor mechanically coupled with a fourth vacuum conveyor, each of the third and fourth vacuum conveyors comprising a movable surface, wherein the movable surface of the third conveyor travels at the second speed and at the first speed, and wherein the movable surface of the fourth vacuum conveyor travels at the first speed, wherein the movable surface of the third vacuum conveyor is in a face-to-face relationship with the movable surface of the second vacuum conveyor, wherein the fourth vacuum conveyor is positioned proximate to the roll surface, wherein the pocket is sized and imparts a bifold in the article in conjunction with manipulation of the article by the first conveyor assembly and the second conveyor assembly.

12. The apparatus of claim 11, wherein the movable surfaces of the first and second vacuum conveyors move away from the roll surface, wherein the movable surfaces of the third and fourth vacuum conveyors move toward the roll surface.

13. The apparatus of claim 11, wherein the movable surfaces of the first, second, third, and fourth vacuum conveyors each comprise a movable foraminous conveyor belt configured in an endless loop.

14. The apparatus of claim 11, wherein a gap is defined between the movable surfaces of the second and third vacuum conveyors, wherein the apparatus further comprises a positioning mechanism, wherein the positioning mechanism adjusts the gap between the second and third vacuum conveyors.

15. An apparatus for transporting articles advancing in a machine direction, wherein each article has a leading end portion and a trailing end portion, the apparatus comprising:

a roll rotatable at a roll speed, the roll comprising a roll surface, the roll surface including a first protrusion and a second protrusion separated by a pocket, wherein the roll surface receives an article, and wherein the leading end portion of the article is disposed on the first protrusion, the trailing end portion of the article is disposed on the second protrusion, and a portion of the article is disposed in the pocket;

a first conveyor assembly comprising a first vacuum conveyor and a second vacuum conveyor, each of the first and second vacuum conveyors including a movable surface, wherein the movable surface of the first vacuum conveyor travels at a first speed and receives the leading end portion of each article from the first protrusion of the roll surface, and wherein the movable surface of the second vacuum conveyor travels at the first speed and at a second speed and receives the leading end portion of each article from the first conveyor; and a second conveyor assembly comprising a third vacuum conveyor and a fourth vacuum conveyor, each of the third and fourth vacuum conveyors comprising a movable surface, wherein the movable surface of the third conveyor travels at the second speed and at the first speed and to receive the leading end portion of each article from the second vacuum conveyor, and wherein the movable surface of the fourth vacuum conveyor travels at the first speed and receives the leading end portion of each article from the third conveyor and transfers the leading end portion of each article to the second protrusion, wherein at least one of the first and second conveyor assemblies includes a positioning mechanism for changing a distance between the movable surfaces of the second and third vacuum conveyors, wherein the pocket is sized and imparts a bifold in the article in conjunction with manipulation of the article by the first conveyor assembly and the second conveyor assembly.

16. The apparatus of claim 15, wherein the pocket has a depth of between 10 millimeters and 150 millimeters.

17. The apparatus of claim 15, wherein the positioning mechanism is mechanically coupled to the movable surface of the third vacuum conveyor.

18. The apparatus of claim 15, wherein the second speed is less than the first speed.

19. The apparatus of claim 15, wherein the first vacuum conveyor and the second vacuum conveyor share a common rotatable shaft.

* * * * *